United States Patent
Sitz et al.

(10) Patent No.: US 6,808,739 B2
(45) Date of Patent: Oct. 26, 2004

(54) DRYING METHOD FOR SELECTIVELY REMOVING VOLATILE COMPONENTS FROM WET COATINGS

(75) Inventors: Richard G. Sitz, Woodbury, MN (US); Peter T. Benson, North St. Paul, MN (US); Kathleen M. Cooklock, Hager City, WI (US); Gary L. Huelsman, St. Paul, MN (US); Nirmal K. Jain, Maple Grove, MN (US); William Blake Kolb, St. Paul, MN (US); John M. Sever, Lino Lakes, MN (US)

(73) Assignee: 3M Innovative Properties Company, St. Paul, MN (US)

( * ) Notice: Subject to any disclaimer, the term of this patent is extended or adjusted under 35 U.S.C. 154(b) by 220 days.

(21) Appl. No.: 09/960,132

(22) Filed: Sep. 21, 2001

(65) Prior Publication Data

US 2002/0100185 A1 Aug. 1, 2002

Related U.S. Application Data

(60) Provisional application No. 60/235,218, filed on Sep. 24, 2000.

(51) Int. Cl.[7] .............................. B05D 1/34; B05D 3/02; A61L 27/00
(52) U.S. Cl. ....................... 427/2.31; 427/2.1; 427/243; 427/372.2; 427/374.2; 427/384; 427/386; 427/391; 427/402; 427/407.1; 427/411; 427/412.5
(58) Field of Search ................................. 427/2.1, 2.31, 427/243, 372.2, 374.2, 384, 386, 391, 402, 407.1, 411, 412.5

(56) References Cited

U.S. PATENT DOCUMENTS

| | | | |
|---|---|---|---|
| RE24,906 E | | 12/1960 | Ulrich |
| 4,053,990 A | | 10/1977 | Bielinski |
| 4,732,808 A | | 3/1988 | Krampe et al. |
| 5,581,905 A | | 12/1996 | Huelsman et al. |
| 5,694,701 A | * | 12/1997 | Huelsman et al. ............ 34/421 |
| 5,980,697 A | | 11/1999 | Kolb et al. |
| 6,010,715 A | * | 1/2000 | Wick et al. ................. 424/448 |
| 6,586,040 B1 | * | 7/2003 | von Falkenhausen ...... 427/2.31 |

FOREIGN PATENT DOCUMENTS

WO     WO 96/08229     * 3/1996

OTHER PUBLICATIONS

Lopez de Ramos, A.L., "Capillary Enhanced Diffusion of $CO_2$ in Porous Media," Ph.D. Thesis, University of Tulsa (1993).

* cited by examiner

Primary Examiner—Shrive P. Beck
Assistant Examiner—Jennifer Kolb Michener
(74) Attorney, Agent, or Firm—Brian E. Szymanski

(57) ABSTRACT

Method of selectively removing volatile components from a composition, comprising coating the composition onto a first substrate surface of a substrate, wherein the composition comprises a nonresident volatile component and a resident volatile component. The method further includes positioning at least a portion of the coated substrate between a condensing surface having a condensing surface temperature and a heating surface having a heating surface temperature that is greater than the condensing surface temperature, wherein the condensing surface is in a spaced apart, confronting relationship to the coated surface of the substrate and wherein the heated surface is in thermal contact with a second substrate surface opposite the first substrate surface. In the method, the heated surface temperature and the condensing surface temperature are such that the positioning step causes the nonresident volatile component to be selectively removed from the portion of the coated substrate. The method is suitable for forming transdermal drug delivery compositions.

22 Claims, 2 Drawing Sheets

DRYING METHOD FOR SELECTIVELY REMOVING VOLATILE COMPONENTS FROM WET COATINGS

TECHNICAL FIELD

This application is claiming priority to U.S. Provisional Application No. 60/235,218, filed Sep. 24, 2000, herein incorporated by reference in its entirety. The present invention relates to a method of selectively removing volatile components from a coated composition. More specifically, the present invention relates to a method of selectively removing one or more volatile components from a coated composition while substantially all of one or more other volatile components remain in the composition. The method of the present invention is particularly suitable for selectively removing solvents from transdermal drug delivery compositions, without removing active ingredients or excipients from the compositions. This allows the composition of the resultant dried coating to be controlled with a high degree of precision.

BACKGROUND OF THE INVENTION

Many products are formed by coating a solvent-containing composition onto a suitable substrate. Such compositions generally include enough solvent so that the composition has a viscosity that allows the composition to be coated onto the substrate at a desired thickness using a desired coating technique. After coating the composition onto the substrate, it is often desirable to remove the solvent to dry the coating.

One drying technique involves heating the coated substrate in an oven to remove the solvent(s) by evaporation. Oven drying typically involves conveying large volumes of heated gas (e.g., air, an inert atmosphere, or the like) through the oven in order to heat and evaporate the solvent(s). As the stream of heated gas is conveyed through the oven, nearly all of the volatile components of the coated composition having a measurable vapor pressure at the drying temperature being used will tend to evaporate from the coating into the heated gas.

Evaporation of any particular volatile component occurs until the partial pressure of that component in the heated gas equals that component's vapor pressure at the surface of the liquid coating, meaning that an equilibrium with respect to that component has been established. However, because of the large volume of heated gas in the chamber at any one time and the fact that fresh heated gas is continuously supplied to the oven during drying, an equilibrium is rarely reached between the heated gas and any volatile component of the coating. As a general consequence, all of the volatile components of the coating tend to continuously evaporate and be carried away in the stream of heated gas throughout the entire drying process.

Of course, when drying is controlled by gas phase mass transfer more volatile components of the coating will evaporate at a faster rate than less volatile components. Nonetheless, evaporation of all the volatile components still occurs even if the drying temperature is well below the boiling point of one or more of the volatile components. In other words, the amount of non-solvent, volatile ingredients in the resultant dried coating will be different, and substantially so in some instances, than the amount of non-solvent volatile ingredients in the initial wet coating. Thus, oven drying offers poor control over the component drying process, because more than just the solvent(s) may be removed from the coating.

The impact of oven drying upon the composition of a dried coating can be illustrated in connection with the manufacture of a transdermal drug delivery device, also known as a transdermal patch. A conventional "peel and place" transdermal patch generally includes a drug-in-adhesive layer sandwiched between an impermeable backing and a release liner. At the time of use, the release liner is removed so that the patch can be attached to a patient, adhesive side down. Over time, the drug in the adhesive layer penetrates into the patient, or is topically active, in furtherance of the desired therapeutic treatment. Optionally, the drug-in-adhesive formulation may include one or more compounds known as penetration enhancers that increase the permeability of the patient's tissue to the drug.

Transdermal patches may be manufactured by coating a suitable substrate (e.g., the release liner, the impermeable backing material, or adhesive coated web, as the case may be) with a coating composition that includes one or more pharmacologically active agents (the drug or drugs, as the case may be), a pressure sensitive adhesive, optionally one or more penetration enhancers, and optionally one or more other excipients. Typically, one or more solvents are also included in the coating composition to facilitate forming a homogeneous coating composition having a suitable coating viscosity. For purposes of illustration, the solvent and the penetration enhancer will be deemed to be the only volatile components of the coating composition, wherein the solvent is substantially more volatile than the penetration enhancer. After such a composition is coated, the solvent is removed to dry the coating. However, because both the solvent and penetration enhancer are volatile components, both the solvent and the penetration enhancer will evaporate upon drying. Thus, a portion of the penetration enhancer in the original formulation is lost during drying. This loss of some of the penetration enhancer during drying is particularly problematic since the drug in adhesive layer of a transdermal patch must often meet tight composition and performance specifications.

Although this discussion of the drug-in-adhesive layer has assumed that only the solvent and the penetration enhancer are volatile components of the coating composition, this might not always be the case. In actual practice, for instance, at least the solvent and any one or more other ingredients of the coating composition may be volatile components.

Knowing that drying often will remove more than just the solvent from a coating being dried, an original coating formulation can include extra amounts of any one or more volatile, non-solvent ingredients in an attempt to compensate for losses that might occur during drying. For example, if a specification requires five weight percent (on a solids basis) of a penetration enhancer in a transdermal patch, but it is known that approximately two weight percent (on a solids basis) of the penetration enhancer might be lost during drying, then the original coating formulation can be formulated with about seven weight percent (on a solids basis) of the penetration enhancer in order to compensate for drying losses. This technique of incorporating extra amounts of ingredients into a coating formulation to compensate for drying losses is often referred to as "over formulation". Over formulation can result in significant cost increase in producing the final product due to the amount of excess materials lost during conventional drying practices.

Accordingly, what is needed is a more accurate approach for drying coatings so that the composition of the resultant dried coating meets precise specifications.

SUMMARY OF THE INVENTION

The present invention relates to a method of selectively removing volatile components from a coated composition. It has now been discovered that the gap drying technique can be used in order to selectively cause some volatile components (i.e., "nonresident" volatile components) to be removed from a coating during drying without removing significant amounts of other volatile components (i.e., "resident" volatile components). In many instances, nonresident ingredients will be the solvents incorporated into a coatable composition. Resident ingredients may be any other ingredients other than the solvent(s).

Gap drying generally involves positioning a coated substrate between a condensing surface and a heating surface. The coated surface of the substrate faces the condensing surface and is separated therefrom by a relatively small gap. The heating surface is in thermal contact with the other side of the coated substrate. The energy from the heating surface is transferred through the substrate to the coating and causes certain components to evaporate from the coating. The resultant vapor travels across the gap above the coating and condenses on the condensing surface. The condensate is collected and removed. Advantageously, the vapor may be condensed, collected, and removed continuously so that the partial pressure of the evaporated component(s) never reaches the corresponding vapor pressure that would be exhibited at steady state equilibrium. As a consequence, the component to be removed from the coating can be continuously evaporated until substantially none of the component remains in the coating.

It has now been discovered that the gap drying process can be used to selectively remove one or more specific volatile components from a coated composition while substantially all of one or more other volatile components remain in the composition. The present invention is able to adapt the gap drying approach to selectively volatilize some components, but not others. This approach is different from conventional convective oven drying carried out at the same heating temperature, because convective oven drying does not selectively volatilize components with the kind of precision provided by gap drying. Gap drying has been described in more detail in U.S. Pat. No. 5,581,905 (Huelsman), U.S. Pat. No. 5,980,697 (Kolb) and U.S. Pat. No. 5,694,701 (Huelsman), incorporated herein by reference in their respective entireties.

Advantageously, selective gap drying in accordance with the present invention allows dried coatings with precise compositions to be formed, because selective gap drying substantially reduces the need to over formulate in order to meet target composition specifications. Except for the solvent(s), the composition to be coated can be formulated at the outset to match the target composition of the dried coating. This ability to precisely match and then maintain the target coating composition is particularly beneficial in connection with the manufacture of transdermal drug delivery compositions which are subject to stringent specifications.

As a concrete example of how the present invention offers improved precision when preparing transdermal drug delivery compositions containing one or more volatile ingredients, the advantages of the present invention may be highlighted in connection with a representative transdermal delivery device suitable for the transdermal delivery of testosterone. Such a device might have a drug-in-adhesive layer whose specification, for purposes of illustration, requires 6 parts by weight testosterone, 23 parts by weight terpineol (boiling point in the range of 214° C. to 224° C.), 2 parts by weight lauramine oxide, and 69 parts by weight of a pressure sensitive adhesive, based upon 100 parts by weight of the dried coating. The specification might further recite that this layer is to be applied from a coating formulation including a solvent of 239.4 parts by weight of ethyl acetate (boiling point of 77° C.) and 26.6 parts of methanol (boiling point of 64.5° C. ) per 6 parts by weight of testosterone. In this particular coating formulation, the terpineol (used as a penetration enhancer), the ethyl acetate (a solvent), and the methanol (a solvent) would be the volatile constituents.

Ordinarily, the above coating formulation might be coated onto a substrate and then dried in an oven in order to remove the solvents, i.e., the ethyl acetate and the methanol. Unfortunately, conventional oven drying would remove not just the solvents, but also substantial portions of the terpineol as well. For example, in order to end up with a dried coating having the specified 23 parts by weight of terpineol when using conventional oven drying, it might be necessary to include as much as 100% more terpineol in order to hit the terpineol target. In other words, 50% of the terpineol included in the original coating formulation is lost during conventional oven drying. Conventionally, the original coating formulation would be over formulated, to compensate for this drying loss. This terpineol loss occurs even if oven drying is carried out at a temperature well below the boiling point of the terpineol, e.g., as low as 66° C.

In contrast, when using selective gap drying according to the present invention, the solvents can be selectively removed from the coating with substantially little impact upon the terpineol content of the coating as the coating dries. For example, if the dried coating is to include 23 parts by weight of terpineol per 6 parts by weight testosterone, then the coating composition may also be formulated with precisely this amount of terpineol. Little (perhaps up to approximately an extra 2% most typically) to no over formulation of terpineol is required because the solvent is selectively removed.

Consequently, the original coating composition (not including solvent) can be formulated at the outset to match the desired dried coating composition. With oven drying, the non-selectivity of the removal of volatile components causes over-formulation in order to compensate for the undesirable loss of material. The utilization of gap drying and the selectivity afforded by the process eliminates over-formulation. Thus the formulator does not have to empirically determine how much terpineol might be lost during oven drying. Dried coatings having target compositions can be formed with great precision as a result.

In one aspect, the present invention relates to a method of selectively removing volatile components from a composition, comprising coating an admixture onto a first substrate surface of a substrate, wherein the admixture comprises one or more volatile solvents, one or more volatile ingredients selected from the group consisting of liquid drugs, liquid excipients and mixtures thereof, and if the volatile ingredient is not therapeutically active, one or more drugs. The method further comprises the step of positioning at least a portion of the coated substrate between a condensing surface having a condensing surface temperature and a heating surface having a heating surface temperature that is greater than the condensing surface temperature, wherein the condensing surface is in a spaced apart, confronting relationship to the coated surface of the substrate and wherein the heated surface is in thermal contact with a second substrate surface opposite the first substrate surface. In the method, the heated surface temperature and the condensing surface temperature are such that the positioning step causes the solvent(s) to be selectively removed from the portion of the coated substrate while substantially all of the volatile ingredient(s) remains in the coated admixture to form the transdermal drug delivery composition.

DETAILED DESCRIPTION OF THE INVENTION

Figure 1:
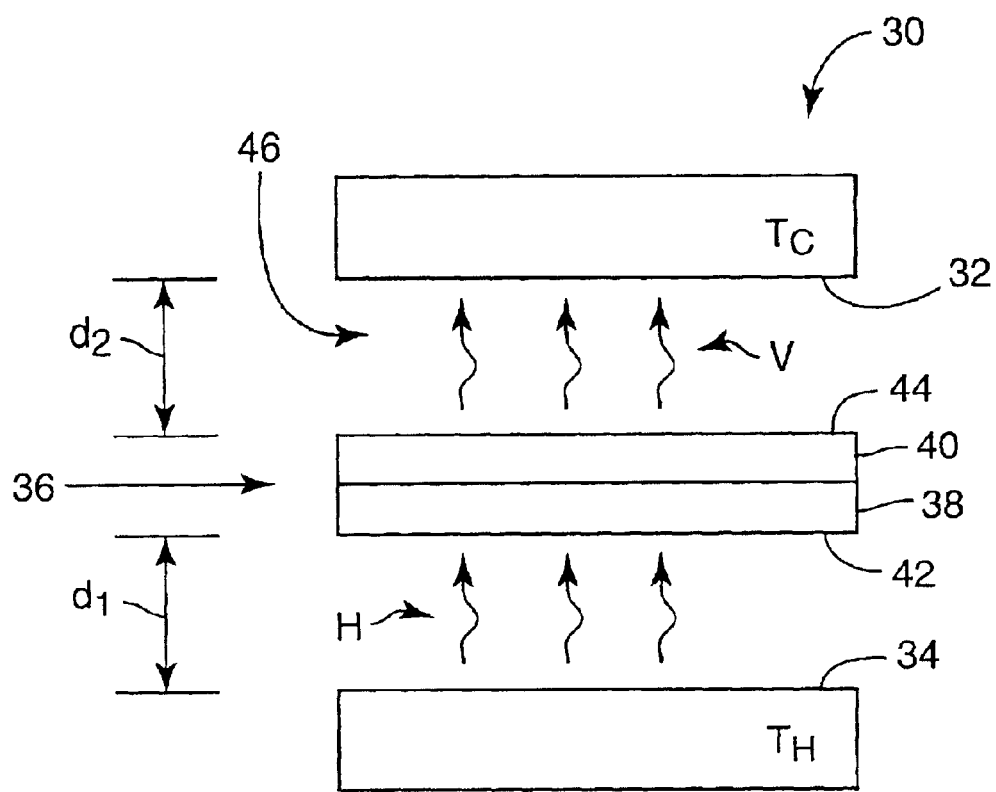
FIG. 1 is a simplified schematic view of a gap drying system that can be used with the present invention.

The embodiments of the present invention described below are not intended to be exhaustive or to limit the invention to the precise forms disclosed in the following detailed description. Rather, the embodiments are chosen and described so that others skilled in the art may appreciate and understand the principles and practices of the present invention.

In the practice of the present invention, a component or ingredient is "volatile" if at 100° C. at least 0.1 mg of the component is released per hour per 10 $cm^2$ of free surface area from a shallow vessel filled with the component when in a substantially unbounded atmosphere of quiescent air at normal pressures. The term "nonresident" will be used to refer to one or more volatile ingredients of a coatable composition that are intended to be removed from the composition when the corresponding coating is dried with the component in a substantially unbounded atmosphere of quiescent air at normal pressures. The term "resident" will be used to refer to one or more volatile ingredients of a coatable composition that are intended to remain in the corresponding dried coating. The term "substantially all" when used in connection with a resident volatile component or ingredient means at least 90 percent by weight of the amount present in the coating composition prior to drying.

The present invention is beneficially used to dry coatings when it is desired to selectively remove one or more nonresident volatile components from the coating during drying without significantly altering the content of the resident volatile components. The present invention is useful, for example, for removing solvents from a repulpable tape composition comprising a volatile neutralizing agent such as methyl diethanol amine. The present invention is also useful for selectively removing solvents during the manufacture of films and reflective sheeting materials comprising volatile plasticizers, ultraviolet light stabilizers, and/or thermal stabilizers. The present invention is particularly useful for selectively removing solvents from transdermal drug delivery compositions comprising one or more resident volatile ingredients.

Examples of nonresident ingredients include solvents such as acetone, ethanol, ethyl acetate, heptane, isopropanol, methanol, methyl ethyl ketone, toluene and mixtures thereof.

Examples of volatile resident ingredients which may be present in a transdermal drug delivery composition include liquid drugs, liquid excipients, and mixtures thereof.

Examples of liquid drugs include nicotine, nitroglycerin, amyl nitrite, ethchlorvynol, paramethadione, scopolamine, and free bases of certain drugs that are conventionally used in the form of acid-addition salts.

Examples of liquid excipients include materials that have been used as penetration enhancers or solubilizers in transdermal drug delivery compositions. Exemplary materials include $C_8$–$C_{22}$ fatty acids such as isostearic acid, octanoic acid and oleic acid; $C_8$–$C_{22}$ fatty alcohols such as oleyl alcohol and lauryl alcohol; $C_8$–$C_{22}$ fatty diols such as lauroglycol; lower alkyl esters of $C_8$–$C_{22}$ fatty acids such as ethyl oleate, isopropyl myristate, butyl stearate and methyl laurate; di(lower)alkyl esters of $C_8$–$C_{22}$ fatty acids such as diisopropyl adipate; monoglycerides of $C_8$–$C_{22}$ fatty acids such as glyceryl monooleate; terpenes such as terpineol; tetraglycol; low molecular weight polyethylene glycols; propylene glycol; 2-(2-ethoxyethoxy)ethanol; diethylene glycol monomethyl ether; and mixtures of the foregoing.

In those instances where the volatile resident ingredient is not therapeutically active i.e., the volatile resident ingredient is an excipient, the wet coating formulation used to prepare a transdermal drug delivery composition will further comprise a drug. Examples of useful drugs include, but are not limited to, antiinflammatory drugs, both steroidal (e.g., hydrocortisone, prednisolone, triamcinolone) and nonsteroidal (e.g., naproxen, piroxicam); bacteriostatic agents (e.g., chlorhexidine, hexylresorcinol); antibacterials (e.g., penicillins such as penicillin V, cephalosporins such as cephalexin, erythromycin, tetracycline, gentamycin, sulfathiazole, nitrofurantoin, and quinolones such as norfloxacin, flumequine, and ibafloxacin); antiprotozoals (e.g., metronidazole); antifungals (e.g., nystatin); coronary vasodilators; calcium channel blockers (e.g., nifedipine, diltiazem); bronchodilators (e.g., theophylline, pirbuterol, salmeterol, isoproterenol); enzyme inhibitors such as collagenase inhibitors, protease inhibitors, elastase inhibitors, lipoxygenase inhibitors (e.g., zileuton), and angiotensin converting enzyme inhibitors (e.g., captopril, lisinopril); other antihypertensives (e.g., propranolol); leukotriene antagonists; anti-ulceratives such as H2 antagonists; steroidal hormones (e.g., progesterone, testosterone, estradiol); antivirals and/or immunomodulators (e.g., imiquimod, resiquimod, acyclovir); local anesthetics (e.g., benzocaine, propofol); cardiotonics (e.g., digitalis, digoxin); antitussives (e.g., codeine, dextromethorphan); antihistamines (e.g., diphenhydramine, chlorpheniramine, terfenadine); narcotic analgesics (e.g., morphine, fentanyl); peptide hormones (e.g., human or animal growth hormones, LHRH); sex hormones (e.g., estrogens, testosterone, progestins such as levonorgestrel, norethindrone, gestodene); cardioactive products such as atriopeptides; proteinaceous products (e.g., insulin); enzymes (e.g., anti-plaque enzymes, lysozyme, dextranase); antinauseants (e.g., scopolomine); anticonvulsants (e.g., carbamazine); immunosuppressives (e.g., cyclosporine); psychotherapeutics (e.g., diazepam); sedatives (e.g., phenobarbital); anticoagulants (e.g., heparin); analgesics (e.g., acetaminophen); antimigraine agents (e.g., ergotamine, melatonin, sumatripan); antiarrhythmic agents (e.g., flecainide); antiemetics (e.g., metaclopromide, ondansetron); anticancer agents (e.g., methotrexate); neurologic agents such as anxiolytic drugs; hemostatics; anti-obesity agents; and the like, as well as pharmaceutically acceptable salts and esters thereof.

In addition to solvents, drug(s) and excipients, the wet coating formulations used to prepare transdermal drug delivery compositions will also generally comprise an adhesive. Examples of suitable adhesives include acrylates, natural and synthetic rubbers such as polyisobutylenes, polysiloxanes, polyurethanes, and other pressure sensitive skin adhesives known in the art. The adhesive polymers can be present alone or in combination. Particularly preferred are the acrylates such as those disclosed in U.S. Pat. No. RE 24,906 (Ulrich), U.S. Pat. No. 4,732,808 (Krampe) and International Publication Number WO 96/08229 (Garbe).

Examples of suitable substrates onto which the wet coating formulation may be coated include backing films, release liners, differential release liners, membranes and any one of the preceding bearing a layer of adhesive.

A representative system 30 for implementing selective gap drying can be described in connection with FIG. 1, which schematically illustrates the selective gap drying process. System 30 includes condensing surface 32 maintained at temperature $T_C$ and heating surface 34 maintained at temperature $T_H$. Condensing surface 32 and heating surface 34 are in a spaced apart, confronting relationship to each other. Article 36 is positioned in between condensing surface 32 and heating surface 34. Article 36 comprises substrate 38 bearing coating 40 to be dried. Heating surface 34 directly faces substrate side 42 of article 36, while condensing surface 32 directly faces coating side 44 of article 36.

Heating surface 34 transfers energy H to substrate 38 and coating 40. Energy H absorbed by coating 40 causes volatile nonresident components of coating 40 to evaporate from coating 40 as vapor V. The temperature $T_H$ of heating surface 34 is controlled so that enough energy H is transferred to coating 40 in order to evaporate the volatile nonresident components of coating 40, but not so much so as to evaporate the volatile resident components of coating 40. In order to reduce blistering in the dried coating, the temperature $T_H$ is preferably within about 20° C. of the boiling point of the volatile nonresident component having the lowest boiling point. More preferably the temperature $T_H$ is within about 10° C. of the boiling point of the volatile nonresident component having the lowest boiling point.

Heating surface 34 is positioned so as to be in thermal contact with article 36. In some cases, thermal contact can be established by placing heating surface 34 in direct physical contact with substrate 38. Alternatively and more preferably, heating surface 34 may be spaced apart from substrate 38 such that substrate 38 and heating surface 34 are not in direct physical contact with each other, but are close enough to each other such that energy H is readily transferred from heating surface 34 to substrate 38 and thence to coating 40. A typical preferred gap distance, $d_1$, between heating surface 34 and substrate 38 is about 0.012 cm to about 0.12 cm.

Condensing surface 32 is spaced apart from, but is in close proximity to, coating 40. This arrangement creates a small, preferably substantially planar gap 46 above coating 40. A typical gap distance, $d_2$, between condensing surface 32 and coating 40 is generally about 0.2 cm to about 0.6 cm. Condensing surface 32 is maintained at a relatively low temperature as compared to heating surface 34 so that vapor V traveling from coating 40 to condensing surface 32 across gap 46 can condense onto surface 32. Generally, condensing surface 32 may be maintained at any temperature, $T_C$, below the dew point of vapor V at a given concentration but above the freezing point of the liquid that condenses on condensing surface 32. Preferably, condensing surface 32 is maintained at a temperature, $T_C$, that is as low as practically possible in order to maximize the rate at which vapor V condenses. Choosing an optimum value of the condensing temperature, $T_C$, may also depend on practical factors such as the nature of the technique that is used to maintain condensing surface 32 at a relatively cool temperature. For example, condensing surface 32 may be maintained at a suitably low temperature, $T_C$, by circulating ice chilled water or other cooling media (not shown) through cooling channels (not shown) located inside condensing surface 32. In such embodiments, condensing surface 32 may be easily maintained at temperatures in the range from about 3° C. to about 10° C.

System 30 of FIG. 1 may be used for selective gap drying in accordance with the present invention. First, condensing surface 32 and heating surface 34 are maintained at the desired temperatures $T_C$ and $T_H$, respectively. Next, coated article 36 bearing coating 40 to be selectively dried is positioned between the condensing surface 32 and the heating surface 34 so that the coating 40 is in a confronting relationship to the condensing surface 32 and the substrate 38 is in thermal contact with the heating surface 34. For purposes of illustration, it will be assumed that coating 40 comprises nonresident volatile component A having a boiling point proximal to $T_H$, i.e., within about 20° C., preferably within about 10° C., and resident volatile component B having a boiling point about 15° C., more preferably 50° C., most preferably 100° C., more than the boiling point of component A. Energy H from heating surface 34 is transferred to coating 40 through the substrate 38. This causes nonresident volatile component A to evaporate as vapor V. Vapor V then condenses on condensing surface 32. This evaporation and condensation process can be continued until substantially all of nonresident volatile component A is volatilized from the coating 40. Energy H, however, causes little, if any, of resident volatile component B to evaporate. The nonresident volatile component A is selectively removed without causing resident volatile component B to evaporate. With convection oven drying, in contrast, a significant portion of resident volatile component B would evaporate from the coating 40.

Figure 2:
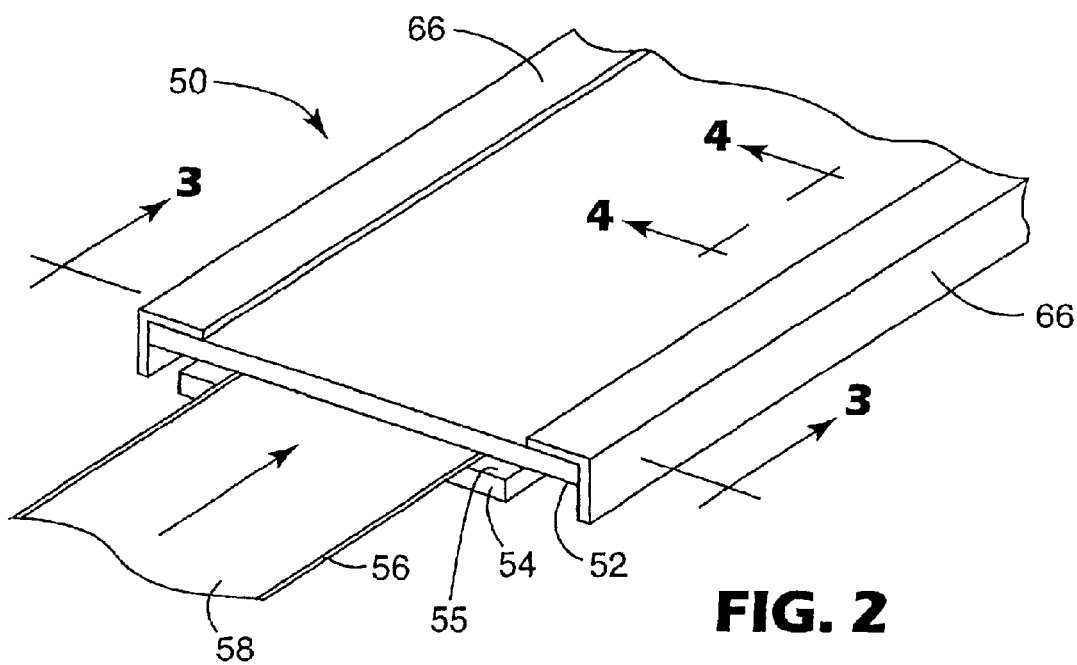
FIG. 2 is a perspective view of a drying apparatus that can be used with the method of the present invention.
Figure 3:
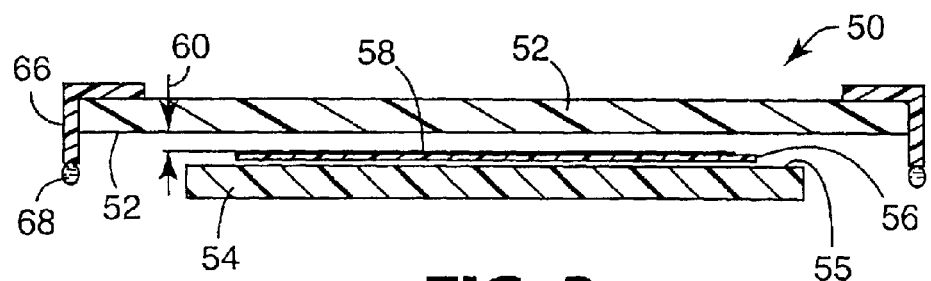
FIG. 3 is a cross-sectional view of the drying apparatus taken along line 3—3 of FIG. 2.

The method of the present invention can be practiced using the gap drying apparatus shown in FIGS. 2 and 3 and also disclosed in U.S. Pat. No. 5,581,905 issued to Huelsman et al., which is herein incorporated by reference in its entirety. As shown in FIGS. 2–3, the drying apparatus 50 includes a condensing platen 52 (which can be chilled) spaced from and in a confronting relationship to a heated platen 54. A web or other substrate 56, having a coating 58, is conveyed between the two platens. Preferably, the web 56 is moved between the platens at a speed in the range of about 5 feet per minute ($2.5 \times 10^{-2}$ meters/second) to about 300 fpm (1.5 m/s) in a conventional manner, e.g., by the use of rollers or the like (not shown). The heated platen 54 is located in a confronting relationship to the non-coated side of the web 56 and has a heating surface 55 that is positioned close enough to the web 56 to be in thermal contact with the non-coated surface of the web 56.

The condensing platen 52 is in a confronting but spaced apart relationship to the coated surface of the web 56. This arrangement creates a small, substantially planar gap 60 above the coated web 56. For example, the condensing platen 52 can be placed about 0.6 cm away from (more preferably, about 0.2 cm away from, or closer) the coated surface of the web 56.

Figure 4:
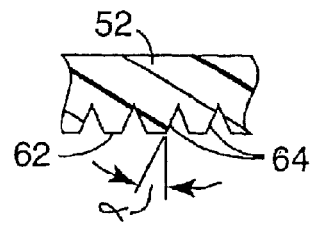
FIG. 4 is a cross-sectional view taken along line 4—4 of FIG. 2.

As shown in FIG. 4, the condensing platen 52 also includes condensing surface 62 having transverse open channels or grooves 64 extending across the width of surface 62 from one edge to the other to thereby form a capillary surface. One type of capillary surface is defined as a geometrically specific surface which satisfies the Concus-Finn Inequality which is: $\alpha + \theta_S < 90°$, where $\alpha$ is half the included angle of any corner and $\theta_F$ is the gas/liquid/solid static contact angle. The static contact angle is governed by the surface tension of the liquid for a given surface material in gas. Capillary surfaces are discussed in great detail in Lopez de Ramos, A. L., "Capillary Enhanced Diffusion of $CO_2$ in Porous Media," Ph.D. Thesis, University of Tulsa (1993). Via capillary forces, liquid that has condensed on the surface 62 is drawn into the grooves and then caused to flow laterally to edge plates 66 (shown in FIGS. 2–3). The condensed liquid can be collected from edge plates 66 for recycling or the like.

For example, as shown in FIGS. 2–3, the force of gravity will overcome the capillary force of the grooves 64 so that the condensed liquid that has collected at the interface of the surface 62 will flow as a film or droplets 68 down the face of the edge plates 66 and fall from the edge plate 66. The falling droplets 68 can be collected in a collecting device (not shown) and recycled or otherwise disposed. This flow of condensed liquid off the plate allows vaporized material to continuously condense on the surface 62 of the condensing platen 52 without the condensed liquid dripping back onto the coated surface of the web 56. To facilitate collection of the condensed liquid, the edge plates 66 can be smooth, capillary surfaces, porous media, or other surfaces. Also, although the edge plates 66 are shown as perpendicular to the condensing surface 62, the edge plates 66 can be at other angles with the condensing surface 62.

The drying apparatus 50 can be used to perform the method of selectively removing nonresident volatile components according to the present invention. First a coating formulation is prepared and is coated by a conventional coating apparatus (not shown) on at least a portion of the web 56 to form the coating 58. The coated portion of the web 56 then can be transported through the drying apparatus 50 by rollers or other conventional transport devices. The coated portion of the web 56 is moved through the drying apparatus 50 by having the web 56 pass between the heating platen 54 and the condensing platen 52 with the coating 58 in a confronting relationship to the condensing platen 52 and the non-coated side of the web 56 in thermal contact with the heating platen 54. Energy from the heating platen 54 heats the coating 58 so that a portion of at least one nonresident volatile component of the coating 58 evaporates and forms a vapor. The vapor travels across the gap 60 formed between the condensing platen 52 and the coating 58 and condenses on the surface 62 of the condensing platen 52, thereby forming a liquid. Capillary forces created by the grooves 64 draw the liquid into the grooves 64 and cause the liquid to flow laterally to edge plates 66. At the interface of the surface 62 and the edge plate 66, the force of gravity will overcome the capillary force of the grooves 64 so that the collected liquid will flow as a film or droplets 68 from the grooves 64, down the face of the edge plates 66, and fall from the edge plate 66, where they can be collected in a collecting device and recycled or otherwise disposed of.

Optionally, the web 56 can be heated by one or more gap dryers in which $T_H$ is varied at least in the direction in which web 56 moves through the dryers. Optionally, vapor V can be condensed in one or more gap dryers in which $T_c$ is varied at least in the direction in which web 56 moves through the dryers. A temperature gradient can be developed across the condensing surface, for example, by using two or more adjacent condensing surfaces that are chilled to different temperatures.

EXAMPLES

Test Methods

Determination of Residual Solvents

The amount of residual ethyl acetate and methanol present in the dried coatings was determined using the following test method.

A 5 $cm^2$ sample is punched from the web and weighed. The release liner is removed from one side and the sample is weighed. The adhesive coating with a release liner still adhered to one surface is placed into an 11 dram (~41 ml) screw cap vial. A 10.0 ml portion of internal standard solution (10 μg/ml of ethanol in N,N-dimethylacetamide) is pipeted into the vial. The vial is securely capped then placed on a laboratory shaker until all of the adhesive coating is dissolved, approximately 4 hours. A portion of the sample is transferred into a 2 ml autosampler vial. The release liner is removed from the sample, allowed to dry and then weighed. The sample in the autosampler vial is analyzed using a suitable gas chromatographic system such as a Hewlett Packard 5890 or 6890 gas chromatograph equipped with a flame ionization detector, autosampler, capillary injection port and an electronic integrator. The chromatographic parameters are: column: 15 m×0.25 mm i.d. J&W Scientific Durabond DB1701, 1.0 μm film thickness; gas flows: carrier: helium at approximately 0.6 ml/min (measured at initial temperature); septum purge flow: approximately 5 ml/min; split vent purge flow: 24.5 ml/min (55:1 split) on at all times; auxiliary makeup flow: 28 ml/min; detector: flame ionization at 280° C.; Oven Temperature Program: initial 45° C., hold 6.0 min, ramp 15° C./min to 280° C., hold 5.0 min; injector: 200° C., 4 mm id, packed split liner with cup; injection volume: 2 μl. Standard solutions containing known amounts of ethyl acetate and methanol with 10 μg/ml ethanol internal standard are prepared and analyzed. Quantitation is performed using internal standard methodology.

Determination of Excipients

The amounts of terpineol, tetraglycol and lauroglycol present in the dried coatings were determined using the following test method.

A 5 $cm^2$ sample is punched from the web and weighed. The release liner is removed from one side of the sample and the sample is weighed. The adhesive coating with one surface still adhered to a release liner is placed into an 11 dram (~41 mil) screw cap vial. A 20.0 ml portion of diluent (90:10 ethyl acetate/methanol) is added to the vial. The vial is securely capped then placed on a laboratory shaker for 1 hour. A 20.0 ml portion of internal standard solution (625 mg/1,000 ml decanol in methanol) is added. The vial is put back on the shaker for 30 minutes. A portion of the sample is removed. The release liner is removed, dried and then weighed. The sample is analyzed using a suitable gas chromatographic system such as a Hewlett Packard 5890 gas chromatograph equipped with a flame ionization detector, autosampler, capillary injection port and an electronic integrator. The chromatographic parameters are: column: 30 m×0.53 mm i.d. J&W Scientific Durabond DB-WAX, P/N 125–7032, 1.0 μm df; gas flows: carrier: helium at approximately 0.6 ml/min (measured at initial temperature); septum purge flow: 2–5 ml/min; split vent purge flow: 228 ml/min (38:1 split) on at all times; auxiliary makeup flow: 24 ml/min; detector: flame ionization at 300° C., attenuation −4; Oven Temperature Program: initial 120° C., hold 0 min, ramp 6° C./min to 225° C., hold 15.0 min; injector: 250° C., 4 mm id, packed split/splitless liner with glass wool plug; chart speed 1.0 cm/min; threshold −4; peak width: 0.16; injection volume: 2 μl. A standard solution containing known amounts of terpineol, tetraglycol and lauroglycol with decanol internal standard is prepared and analyzed. Quantitation is performed using internal standard methodology.

Preparation of Coating Formulations

A coating formulation (Formulation 1) was prepared by combining 26587.6 g of wet adhesive (73/7/20 w/w/w isooctyl acrylate/acrylamide/vinyl acetate adhesive copolymer at 22% solids in 90/10 w/w ethyl acetate/methanol), 179.4 g of terpineol, and 15.6 g of lauramine oxide and mixing on a roller mixer to provide a homogeneous coating formulation. Using the same general method, two additional coating formulations were prepared. Table 1 below summarizes the amount (weight percent) and identity of the components of each formulation. The table also shows the "theoretical dry" composition which is calculated based on the assumption that all of the solvent (ethyl acetate and methanol) is removed on drying but all of the other components remain.

TABLE 1

| Component | Formulation 1 (w %) | | Formulation 2 (w %) | | Formulation 3 (w %) | |
|---|---|---|---|---|---|---|
| | Wet | Theoretical Dry | Wet | Theoretical Dry | Wet | Theoretical Dry |
| Terpineol | 6.28 | 22.99 | 2.51 | 9.00 | | |
| Lauramine oxide | 0.55 | 2.01 | | | | |
| Tetraglycol | | | 2.51 | 9.00 | 4.33 | 16.00 |
| Lauroglycol | | | 2.51 | 9.00 | 2.17 | 8.02 |
| Copolymer[1] | 20.49 | 75.00 | 20.35 | 72.99 | 20.57 | 75.99 |
| Ethyl acetate | 65.41 | | 64.91 | | 65.65 | |
| Methanol | 7.27 | | 7.22 | | 7.28 | |

[1]73/7/20 w/w/w isooctyl acrylate/acrylamide/vinyl acetate

The experiments described in Examples 1–23 below were conducted using a two section "gap" dryer. Each section was 5 feet (1.5 m) long. The first section was 10 inches (25.4 cm) wide and had an 80 foot (24 meter) radius curvature. The second section was 8 inches (20.3 cm) wide and was flat.

Heating was provided to the lower platens in each section by two independent hot water recirculating units with individual controls. Cooling was provided to the upper platens by two independent chillers with individual controls using a 50% propylene glycol recirculating mixture. The gap between the upper and lower platens was set at 1/8 inch (0.32 cm) throughout the length of each section. The capillary grooves were 0.1 cm deep, with a 0.15 cm peak-to-peak distance, a 0.1 cm land at the top and bottom of the grooves, and were rectangular in shape.

Examples 1–9

Formulation 1 was coated at a width of 5 inches (12.7 cm) onto a 5 mil (127 μm) thick polyester web using a fluid bearing die with a 10 mil (254 μm) shim. The coating formulation was transferred to the die using a Zenith positive displacement gear pump with a volumetric number of 20 cubic centimeters of liquid per revolution. The coated web was dried. The exposed surface was covered with a release liner. Samples were then tested for residual solvents and terpineol content using the test methods described above. Table 2 below summarizes the process conditions used for preparing each example and the resulting levels of residual solvent and terpineol.

The results shown in Table 2 below demonstrate the ability of the method of the invention to selectively remove solvents while leaving substantially all of the penetration enhancer in the dried coating. The combined solvents (ethyl acetate and methanol) represent 73% of the weight of the wet formulation; in the dried coating the solvents are present in a range of 0.1 to 3% by weight. Terpineol was present at 6.28% by weight in the wet formulation; in the dried coating it is present in a range of 21 to 22% by weight.

TABLE 2

| | Process Conditions | | | | Results | | | |
|---|---|---|---|---|---|---|---|---|
| | Platen Temperature (° C.) | | Line Speed | Pump Speed | Coating Weight | Solvent/Excipient Content (mg/g) | | |
| Example Number | Lower | Upper | (m/s) | (rpm) | (mg/cm[2]) | Ethyl Acetate | Methanol | Terpineol |
| 1 | 79/79* | 8/8 | 0.006 | 4.5 | 28 | 28.45 | 0.721 | 211 |
| 2 | 79/79 | 8/8 | 0.013 | 4.5 | 13.5 | 3.24 | 0.260 | 222 |
| 3 | 79/79 | 8/8 | 0.025 | 9 | 13.4 | 22.90 | 0.538 | 222 |
| 4 | 79/79 | 8/8 | 0.051 | 9 | 6.51 | 0.714 | 0.436 | 224 |
| 5 | 79/79 | 8/8 | 0.101 | 18 | 7.12 | 1.45 | 0.394 | 225 |
| 6 | 79/79 | 8/8 | 0.038 | 13.5 | 15.95 | 24.36 | 0.528 | 224 |
| 7 | 79/79 | 8/8 | 0.051 | 18 | Did not dry well enough to sample | | | |
| 8 | 79/93 | 8/8 | 0.038 | 13.5 | 15.19 | 29.30 | 0.528 | 218 |
| 9 | 79/93 | 16/16 | 0.038 | 13.5 | 14.86 | 15.64 | 0.352 | 221 |

*Section 1/Section 2 of the dryer

Examples 10–16

Formulation 2 was coated at a width of 5 inches (12.7 cm) onto a 2 mil (51 μm) thick polyester silicone coated release liner using a fluid bearing die with a 10 mil (254 μm) shim. The coating formulation was transferred to the die using a Zenith positive displacement gear pump with a volumetric number of 10 cubic centimeters of liquid per revolution. The coated liner was dried. The exposed surface was covered with a release liner. Samples were tested for residual solvents and excipient content using the test methods described above. Table 3 below summarizes the process conditions used for preparing each example and the resulting levels of residual solvent and excipients. In all instances the temperature of both lower platens was maintained at 80° C. and that of both upper platens was maintained at 5° C.

The results shown in Table 3 below demonstrate the ability of the method of the invention to selectively remove solvents. While the combined solvents (ethyl acetate and methanol) represent 72% of the weight of the wet formulation; in the dried coating the solvents are present in a range of 0.3 to 9% by weight. Terpineol was present at 2.5% by weight in the wet formulation; in the dried coating it is present in a range of 8.2 to 9.2% by weight. Lauroglycol was present at 2.5% by weight in the wet formulation; in the dried coating it is present in a range of 8.2 to 9.5% by weight. Tetraglycol was present at 2.5% by weight in the wet formulation; in the dried coating it is present in a range of 8.2 to 9.4% by weight.

TABLE 3

| | Process Conditions | | | Results | | | | |
|---|---|---|---|---|---|---|---|---|
| | Line | Pump | Coating | Solvent/Excipient Content (mg/g) | | | | |
| Example Number | Speed (m/s) | Speed (rpm) | Weight (mg/cm$^2$) | Ethyl Acetate | Methanol | Terpineol | Lauro-glycol | Tetraglycol |
| 10 | 0.051 | 10.2 | 6.73 | 2.80 | — | 89.1 | 94.7 | 93.6 |
| 11 | 0.102 | 20.4 | 7.73 | 87.45 | 1.13 | 81.6 | 82.3 | 82.5 |
| 12 | 0.203 | 30 | 6.09 | 2.14 | 0.20 | 91.8 | 94.2 | 94.4 |
| 13 | 0.051 | 14 | 10.00 | 3.46 | 0.14 | 87.0 | 92.3 | 93.1 |
| 14 | 0.102 | 23.5 | 9.91 | 61.04 | 1.07 | 83.9 | 85.5 | 85.1 |
| 15 | 0.013 | 5 | 12.87 | 2.56 | 0.20 | 84.1 | 92.6 | 93.8 |
| 16 | 0.025 | 9.5 | 13.19 | 47.38 | 0.84 | 82.8 | 87.7 | 86.9 |

Examples 17–23

Formulation 3 was coated at a width of 5 inches (12.7 cm) onto a 2 mil (51 μm) thick polyester silicone coated release liner using a fluid bearing die with a 10 mil (254 μm) shim. The coating formulation was transferred to the die using a submersed Zenith positive displacement gear pump with a volumetric number of 10 cubic centimeters of liquid per revolution. The coated liner was dried. The exposed surface was covered with a release liner. Samples were tested for residual solvents and excipient content using the test methods described above. Table 4 below summarizes the process conditions used for preparing each example and the resulting levels of residual solvent and excipients. In all instances the temperature of both lower platens was maintained at 80° C. and that of both upper platens was maintained at 5° C.

The results shown in Table 4 below demonstrate the ability of the method of the invention to selectively remove solvents. While the combined solvents (ethyl acetate and methanol) represent 73% of the weight of the wet formulation; in the dried coating the solvents are present in a range of 0.1 to 5% by weight. Lauroglycol was present at 2.2% by weight in the wet formulation; in the dried coating it is present in a range of 6.7 to 8.6%. Tetraglycol was present at 4.3% by weight in the wet formulation; in the dried coating it was present in a range of 13.2 to 16.4% by weight.

The experiments described in Comparative Examples 1–8 below were conducted using conventional impingement drying equipment. A Hirano Multi-Coater with two ovens was used. The first oven was 5 ft (1.5 m) long and had an air gap (the vertical distance between the top and bottom nozzles) of 0.75 inches (1.9 cm). The second oven was 5.5 ft (1.7 m) long and had an air gap of 0.5 inches (1.3 cm). The first oven had five nozzles on the top and five on the bottom. The second oven has six nozzles on the top and five on the bottom. All nozzles were of the flotation design type (i.e. two slots on each nozzle running the entire nozzle length).

Comparative Examples 1–6

The formulation was knife coated at a width of 5.25 inches (13.3 cm) onto a 3 mil (76 μM) thick differential release liner. The coating gap was set at 37 mils (940 μM) for Examples 1–4, 36 mils (914 μM) for Example 5 and 40 mils (1016 μM) for Example 6. The coated web was dried. The exposed surface was covered with a release liner. Samples were tested for residual solvent and excipient content using the test methods described above. Table 5 below summarizes the process conditions used for preparing each example and the resulting levels of residual solvent and excipients. In all instances the line speed was 0.43 m/min and the temperature in both ovens was 150° F. (66° C.).

The results in Table 5 below demonstrate that while conventional impingement drying can successfully remove solvents, the desired excipients, particularly those that are not high boiling, will also be at least partially removed. In Comparative Examples 1 and 2, the terpineol level is 15 and 11% respectively which is well below the target level of 23%. In contrast, when the same formulation was dried using the method of the invention (Examples 1–9), the terpineol level is in the range of 21 to 22%. In Comparative Examples 3 and 4, the terpineol level is 5.3 and 3.5% respectively which is well below the target level of 9.0%. In contrast, when the same formulation was dried using the method of the invention (Examples 10–16), the terpineol level is in the range of 8.2 to 9.2%.

TABLE 4

| | Process Conditions | | | Results | | | |
|---|---|---|---|---|---|---|---|
| | Line | Pump | Coating | Solvent/Excipient Content (mg/g) | | | |
| Example Number | Speed (m/s) | Speed (rpm) | Weight (mg/cm$^2$) | Ethyl Acetate | Methanol | Lauro-glycol | Tetraglycol |
| 17 | 0.051 | 11 | 6.34 | 0.811 | 0.277 | 85.9 | 164 |
| 18 | 0.102 | 21 | 6.27 | 1.979 | 0.238 | 84.2 | 162 |
| 19 | 0.203 | 35 | 6.58 | 7.052 | 0.510 | 85.6 | 164 |
| 20 | 0.051 | 16.5 | 10.65 | 30.30 | 0.619 | 73.9 | 145 |
| 21 | 0.102 | 26.5 | 9.33 | 46.40 | 0.842 | 66.8 | 132 |
| 22 | 0.025 | 11.5 | 14.99 | 41.32 | 0.818 | 74.8 | 147 |
| 23 | 0.013 | 6 | 14.19 | 3.674 | 0.217 | 80.8 | 158 |

|  |  | Oven 1 | Oven 2 | | Results | | | | |
| --- | --- | --- | --- | --- | --- | --- | --- | --- | --- |
|  |  | Air | Air | Coating | Solvent/Excipient Content (mg/g) | | | | |
| Example Number | Formulation Number | Velocity (m/s) | Velocity (m/s) | Weight (mg/cm$^2$) | Ethyl Acetate | Methanol | Terpineol | Lauro-glycol | Tetraglycol |
| C1 | 1 | 16.4 | 15.9 | 12.53 | 7.103 | 0.305 | 151 |  |  |
| C2 | 1 | 31.6 | 29.9 | 10.23 | 1.149 | 0.221 | 114 |  |  |
| C3 | 2 | 16.4 | 15.9 | 13.08 | 2.661 | 0.317 | 53.4 | 84.2 | 87.1 |
| C4 | 2 | 31.6 | 29.9 | 10.85 | 0.401 | 0.337 | 35.3 | 77.2 | 93.3 |
| C5 | 3 | 16.4 | 15.9 | 11.83 | 1.126 | 0.359 |  | 135 | 78.7 |
| C6 | 3 | 31.6 | 29.9 | 15.2 | 8.931 | 0.365 |  | 140 | 72.4 |

Comparative Examples 7 and 8

A variation of formulation 1 in which terpineol was "over formulated" i.e., the amount of terpineol in the wet formulation was increased from 6.28% to 9.14%, was prepared. The formulation was knife coated at a width of 5.25 inches (13.3 cm) onto a 3 mil (76 µM) thick differential release liner. The coating gap was set at 37 mils (940 µM). The coated web was dried. The exposed surface was covered with a release liner. Samples were tested for residual solvent and excipient content using the test methods described above. Table 6 below summarizes the process conditions used for preparing each example and the resulting levels of residual solvent and excipients. In all instances the line speed was 0.43 m/min and the temperature in both ovens was 150° F. (66° C.).

The results in Table 6 below demonstrate that even with an over formulation of terpineol by about 45% the terpineol content of the coatings dried by conventional impingement drying was below the target level.

|  |  |  |  | Results | | |
| --- | --- | --- | --- | --- | --- | --- |
|  |  |  |  | Solvent/Excipient Content (mg/g) | | |
| Example Number | Oven 1 Air Velocity (m/s) | Oven 2 Air Velocity (m/s) | Coating Weight (mg/cm$^2$) | Ethyl Acetate | Methanol | Terpineol |
| C7 | 16.4 | 15.9 | 14.05 | Not run | Not run | 209.6 |
| C8 | 31.6 | 29.9 | 11.49 | 7.98 | 0.325 | 176.2 |

Other embodiments of this invention will be apparent to those skilled in the art upon consideration of this specification or from practice of the invention disclosed herein. Various omissions, modifications, and changes to the principles and embodiments described herein may be made by one skilled in the art without departing from the true scope and spirit of the invention which is indicated by the following claims.

What is claimed is:

1. A method of selectively removing volatile components from a composition, comprising:
   coating a coating formulation onto a first substrate surface of a substrate, wherein the coating formulation comprises solvent, one or more volatile ingredients selected from the group consisting of liquid drugs, liquid excipients and mixtures thereof, and if the volatile ingredient is not therapeutically active, one or more drugs;
   positioning at least a portion of the coated substrate between a condensing surface having a condensing surface temperature and a heating surface having a heating surface temperature that is greater than the condensing surface temperature, wherein the condensing surface is in a spaced apart, confronting relationship to the coated surface of the substrate and wherein the heated surface is in thermal contact with a second substrate surface opposite the first substrate surface; and
   wherein the heated surface temperature and the condensing surface temperature are such that the positioning causes the solvent to be selectively removed from the portion of the coated substrate.

2. The method of claim 1, wherein substantially all of the resident volatile component remains in the portion of the coated substrate.

3. The method of claim 1, wherein the heating surface temperature is within about 20° C. of the boiling point of the solvent having the lowest boiling point.

4. The method of claim 3, wherein the heating surface temperature is within about 10° C. of the boiling point of the solvent having the lowest boiling point.

5. The method of claim 1, wherein the heating surface has a temperature gradient in which the heating surface temperature increases along the temperature gradient in the longitudinal direction of the heating surface, and wherein the positioning further comprises moving the substrate along the temperature gradient in the longitudinal direction of the heating surface so that successive portions of the substrate come into thermal contact with the heating surface.

6. The method of claim 1, wherein the positioning comprises positioning the substrate within about 1 cm of the condensing surface.

7. The method of claim 1, further comprising:
   condensing the vapor on the condensing surface to create a condensate; and removing the condensate from the condensing surface while the condensate remains in the liquid state.

8. The method of claim 7, further comprising recovering and collecting the condensate removed from the substrate.

9. The method of claim 1, wherein the solvent is acetone, ethanol, ethyl acetate, heptane, isopropanol, methanol, methyl ethyl ketone, toluene or mixtures thereof.

10. The method of claim 1, wherein the volatile ingredient is a liquid drug.

11. The method of claim 10, wherein the drug is nicotine, nitroglycerin or scopolamine.

12. The method of claim 1, wherein the volatile ingredient is a liquid excipient.

13. The method of claim 12, wherein the excipient is $C_8$–$C_{22}$ fatty acids, $C_8$–$C_{22}$ fatty alcohols, $C_8$–$C_{22}$ fatty diols, lower alkyl esters of $C_8$–$C_{22}$ fatty acids, di(lower) alkyl esters of $C_8$–$C_{22}$ fatty acids, monoglycerides of $C_8$–$C_{22}$ fatty acids, terpenes, tetraglycol, polyethylene glycol ether, polyethylene glycol, propylene glycol, 2-(2-ethoxyethoxy)ethanol, diethylene glycol monomethyl ether or mixtures thereof.

14. The method of claim 13, wherein the excipient is oleyl alcohol, lauryl alcohol, isopropyl myristate, ethyl oleate, methyl laurate, diisopropyl adipate, glyceryl monolaurate, terpineol, tetraglycol, polyethylene glycol, propylene glycol, 2-(2-ethoxyethoxy)ethanol, diethylene glycol monomethyl ether or mixtures thereof.

15. The method of claim 1, wherein the drug is testosterone.

16. The method of claim 1, wherein the coated substrate is a transdermal drug delivery composition.

17. The method of claim 16, wherein the transdermal drug delivery composition further comprises an adhesive.

18. The method of claim 1, wherein the coating formulation further comprises an adhesive.

19. The method of claim 18, wherein the adhesive is an acrylate.

20. The method of claim 1, wherein the substrate comprises a release liner.

21. The method of claim 1, wherein the substrate comprises a backing film.

22. A method of forming a transdermal drug delivery composition, comprising:

coating a coating formulation onto a first substrate surface of a substrate, wherein the coating formulation comprises solvent, one or more volatile ingredients selected from the group consisting of liquid drugs, liquid excipients and mixtures thereof, and if the volatile ingredient is not therapeutically active, one or more drugs, positioning at least a portion of the coated substrate between a condensing surface having a condensing surface temperature and a heating surface having a heating surface temperature that is greater than the condensing surface temperature, wherein the condensing surface is in a spaced apart, confronting relationship to the coated surface of the substrate and wherein the heated surface is in thermal contact with a second substrate surface opposite the first substrate surface; and wherein the heated surface temperature and the condensing surface temperature are such that the positioning causes the solvent to be selectively removed from the portion of the coated substrate such that substantially all of the resident volatile component remains in the portion of the coated substrate.

* * * * *

UNITED STATES PATENT AND TRADEMARK OFFICE
CERTIFICATE OF CORRECTION

PATENT NO. : 6,808,739 B2
DATED : October 26, 2004
INVENTOR(S) : Sitz, Richard G.

It is certified that error appears in the above-identified patent and that said Letters Patent is hereby corrected as shown below:

Column 8,
Line 42, "comer and $\theta_F$" should be shown as -- corner and $\theta_S$ --

Column 12,
Table 2, under Solvent/Excipient Content (mg/g);
  "Ethyl

Acetate   Methanol   Terpineol" should be shown as
-- Ethyl
Acetate   Methanol   Terpineol --

Column 15,
Lines 1-15, first Table, please insert the heading for this table as -- TABLE 5 --
Lines 40-45, first Table, please insert the heading for this table as -- TABLE 6 --

Signed and Sealed this

Twelfth Day of April, 2005

JON W. DUDAS
*Director of the United States Patent and Trademark Office*